(12) United States Patent
Olson

(10) Patent No.: US 8,636,808 B2
(45) Date of Patent: Jan. 28, 2014

(54) SPHERICAL SUBTALAR IMPLANT

(75) Inventor: Jon Olson, Houston, TX (US)

(73) Assignee: Trilliant Surgical, Ltd., Houston, TX (US)

( * ) Notice: Subject to any disclaimer, the term of this patent is extended or adjusted under 35 U.S.C. 154(b) by 113 days.

(21) Appl. No.: 13/011,330

(22) Filed: Jan. 21, 2011

(65) Prior Publication Data
US 2012/0191209 A1 Jul. 26, 2012

Related U.S. Application Data

(62) Division of application No. 13/011,243, filed on Jan. 21, 2011, now Pat. No. 8,545,572.

(51) Int. Cl.
*A61F 2/42* (2006.01)
(52) U.S. Cl.
USPC .................... 623/21.18; 623/21.11
(58) Field of Classification Search
USPC ............... 606/289, 300, 314, 310; 623/21.11–21.19; 411/423, 411
See application file for complete search history.

(56) References Cited

U.S. PATENT DOCUMENTS

| 5,246,441 A * | 9/1993 | Ross et al. ............... 606/53 |
| 6,572,315 B1 * | 6/2003 | Reed ....................... 411/307 |
| 7,033,398 B2 | 4/2006 | Graham |
| 7,678,153 B2 | 3/2010 | Katz et al. |
| 2008/0177331 A1 * | 7/2008 | Perez-Cruet et al. ...... 606/301 |

FOREIGN PATENT DOCUMENTS

WO    WO 0069352 A1 * 11/2000

OTHER PUBLICATIONS

"Correspondence from Scott Houtteman," dated Sep. 8, 2012, 7 pages.
Integra, "Proven Titanium Subtalar Implant, Subtalar MBA Implant System," 2010, 1 page.
Tornier DX—Futura Subtalar Implants, "Subtalar Implants," 2010, 6 pages.

* cited by examiner

*Primary Examiner* — Bruce E Snow
*Assistant Examiner* — Brian Dukert
(74) *Attorney, Agent, or Firm* — Trop, Pruner & Hu, P.C.

(57) ABSTRACT

One embodiment of the invention includes a sinus tarsi implant with a proximal portion that includes a spherical portion. The spherical portion may include apertures for tissue in-growth. The implant design limits patient discomfort due to pressure points. Other embodiments are disclosed.

15 Claims, 7 Drawing Sheets

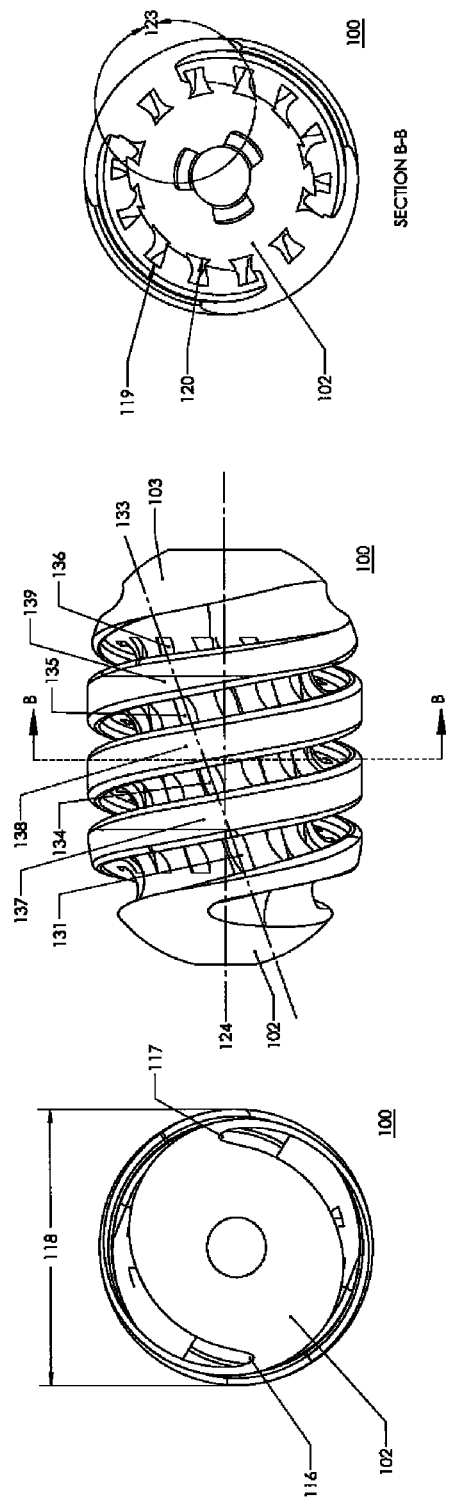

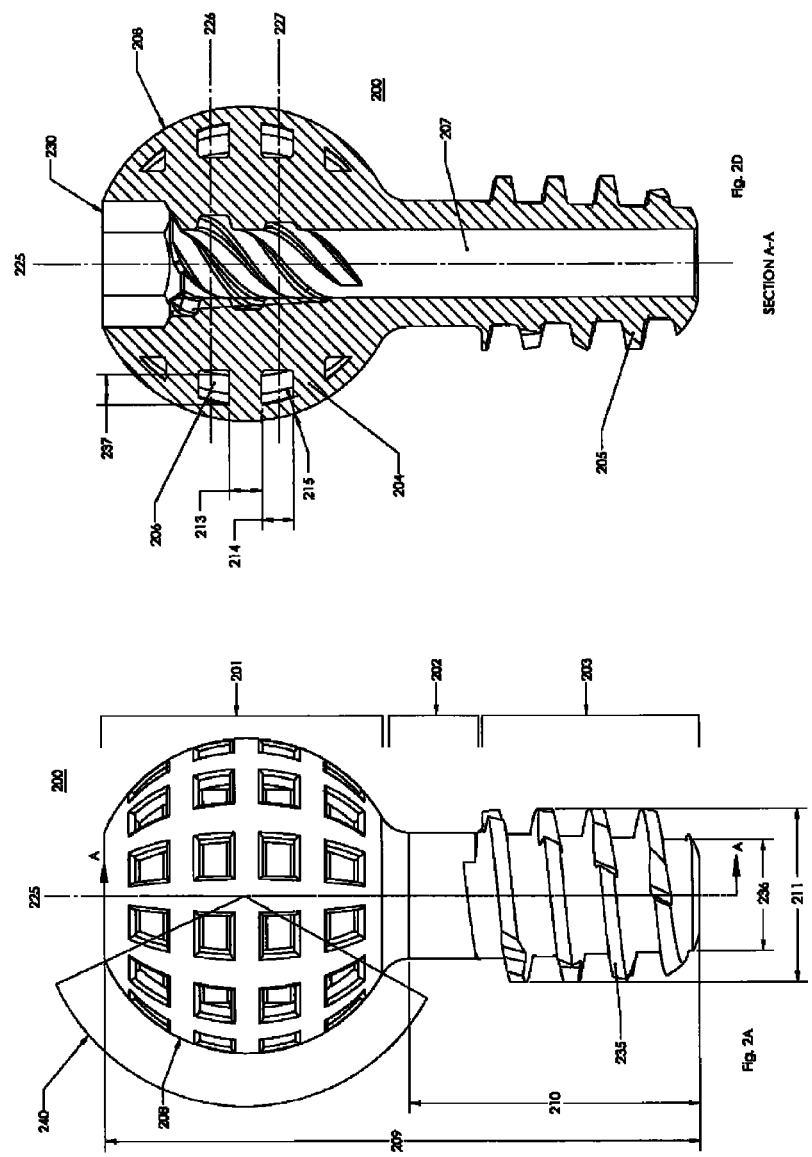

US 8,636,808 B2

SPHERICAL SUBTALAR IMPLANT

This application claims priority to and is a divisional of U.S. patent application Ser. No. 13/011,243 filed on Jan. 21, 2011 now U.S. Pat. No. 8,545,572 and entitled "SUBTALAR IMPLANT", the content of which is hereby incorporated by reference.

BACKGROUND

Subtalar Arthroesis implants, also known as sinus tarsi implants, help treat the hyperpronated foot by stabilizing the subtalar joint. The implant may be designed to block forward, downward, and/or medial displacement of the talus, thereby allowing normal subtalar joint motion while limiting excessive pronation.

Subtalar implants, however, often "back out" or "migrate" from their original implant locations. To mitigate migration, the thread profile of subtalar implants may be aggressive or "deep" to increase the "negative space" of the thread and provide for deeper coupling with tissue. A negative thread space includes, for example, the troughs between the thread crests. In other words, the negative thread space includes the space bordered by the main bodies of two adjacent threads, the core body of the device, and a line connecting the crests of the two adjacent threads. The thread crests are the lateral tips or "crests" of the threads.

However, to create the thread profile for the deep negative space a lathe typically removes significant amounts of material from the thread crest. For example, with conventional thread forms the thread tapers from a wider base to a thinner thread crest. Consequently, machining a larger or deeper negative space requires the removal of additional thread crest area proportionally. As the amount of thread crest surface area decreases the inherent load upon the implant is more focused. This focused load results in higher stress levels for the tissue/implant interface (e.g., pressure points), which may lead to patient discomfort and implant removal.

Pressure points are not caused only by low surface area thread crests. Pressure points may also arise from the general shape of the proximal portion of subtalar implants. For example, conical shaped implants may flare out laterally as the proximal end of the implant is approached. However, the conical shape (as well as cylindrical portions of implants) often terminates proximally in a dramatic non-rounded fashion, thereby leaving a sharp or low-surface area edge and a corresponding pressure point that may possibly be painful.

BRIEF DESCRIPTION OF THE DRAWINGS

Features and advantages of embodiments of the present invention will become apparent from the appended claims, the following detailed description of one or more example embodiments, and the corresponding figures, in which:

FIG. 1D includes a plan view of one embodiment of the invention.

FIG. 1E includes a side view of one embodiment of the invention.

FIG. 1F includes a plan view of one embodiment of the invention.

FIG. 2A includes a side view of one embodiment of the invention.

FIG. 2D includes a section view of one embodiment of the invention.

DETAILED DESCRIPTION

In the following description, numerous specific details are set forth. However, it is understood that embodiments of the invention may be practiced without these specific details. Well-known structures and techniques have not been shown in detail to avoid obscuring an understanding of this description. References to "one embodiment", "an embodiment", "example embodiment", "various embodiments" and the like indicate the embodiment(s) so described may include particular features, structures, or characteristics, but not every embodiment necessarily includes the particular features, structures, or characteristics. Further, some embodiments may have some, all, or none of the features described for other embodiments. Also, as used herein "first", "second", "third" describe a common object and indicate that different instances of like objects are being referred to. Such adjectives are not intended to imply the objects so described must be in a given sequence, either temporally, spatially, in ranking, or in any other manner. Also, the terms "coupled" and "connected," along with their derivatives, may be used. In particular embodiments, "connected" may be used to indicate that two or more elements are in direct physical or electrical contact with each other and "coupled" may mean that two or more elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

One embodiment of the invention includes a sinus tarsi implant with an inverted thread profile (e.g., having a thread profile that widens towards the thread crest) having a lip or lips at the thread crest. The lips may help hold tissue in-growth and give greater purchase to the implant. The implant may also include voids that traverse threads. The voids may create an open area for tissue (e.g., bone, soft tissue) to grow into. The voids may be relatively small and consequently promote faster tissue in-growth. Thus, the lips and/or voids limit migration. They do this without creating (or at least limiting) sharp edges or pressure points on thread crests that are typically associated with techniques (e.g., deep negative thread spaces) used to prevent migration. Therefore, the embodiments of the invention limit migration while also limiting patient discomfort.

Figure 1C:
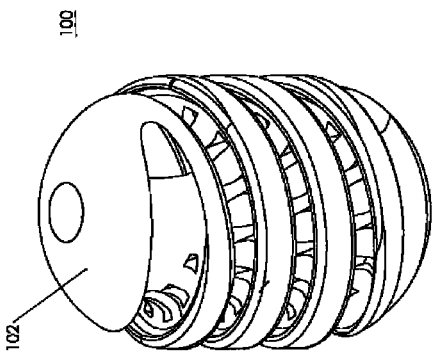
FIG. 1C includes a perspective view of one embodiment of the invention.
Figure 1B:
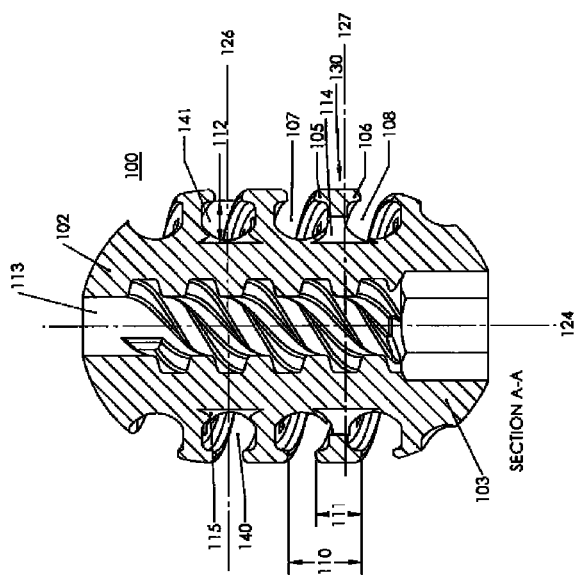
FIG. 1B includes a section view of one embodiment of the invention.
Figure 1A:
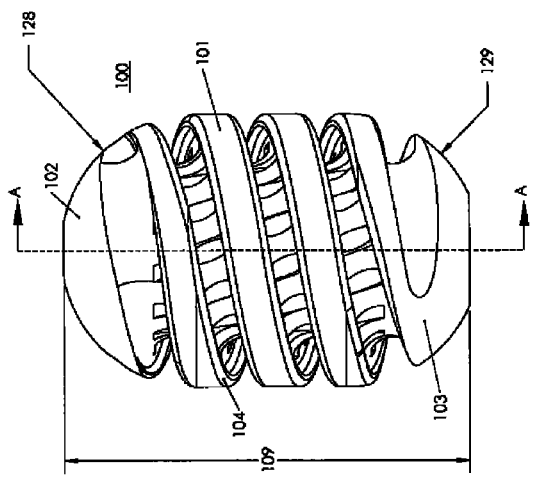
FIG. 1A includes a side view of one embodiment of the invention.
Figure 1H:
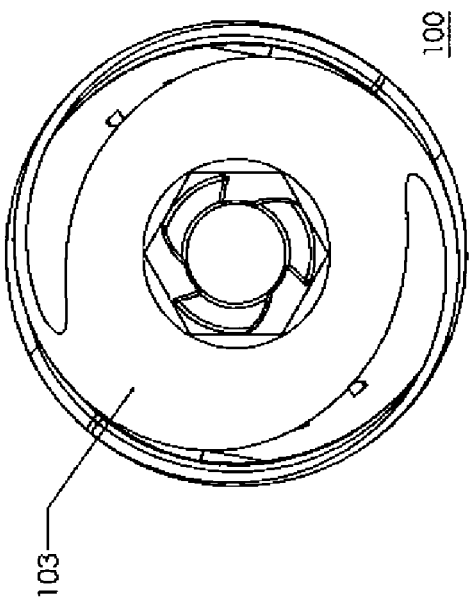
FIG. 1H includes a plan view of one embodiment of the invention.

FIGS. 1A-B include a subtalar implant 100 that includes a cannulated main body having a middle portion connected between proximal end 103 and distal end 102. Distal end 102 is the leading edge that inserts into a sinus. Central hollow shaft 113 extends from proximal end 103 to distal end 102 defining longitudinal axis 124. Thread 101 revolves about implant 100 and includes thread crest 130 located adjacent to negative thread space 107 and negative thread space 108. In one embodiment, thread crest 130 includes lip 105 projecting across a portion of negative thread space 107 and lip 106, opposite lip 105, projecting across a portion of negative thread space 108. In an embodiment thread 101 may include beveled edge 104. As used herein, thread crest 130 describes a portion of the crest for thread 101, which rotates about implant 100.

In an embodiment, lips 105, 106 are manufactured without use of a lathe. Instead, device 100 may be manufactured using titanium or titanium alloy powder and a 3D printer, such as a Direct Metal Laser Sintering (DMLS) or Electron Beam Machining (EBM) device. In an embodiment, lips or flanges 105, 106 may be thought to form a lateral end of the thread shaped in a "T" formation. This "T" formation may also be thought to include elements of an "I" beam wherein the lips correspond to the I beam flanges and the main thread body corresponds to the web of the I beam. As such, the main thread body (i.e., the web or portion leading laterally towards the crest) may resist shear forces while the flanges or lips resist bending moments experienced by the thread. Thus, the I beam thread efficiently carries bending and shear loads that may be experienced by implant 100.

However, embodiments are not limited to this configuration and may include, for example, "L" forms where only 1 lip is included. Also, embodiments do not necessarily require lips at all. Further, the lips need not be symmetrical. For example, lip 105 may be larger than lip 106. Also, the lips may offset from the main thread body at different angles. Also, while the lips are generally orthogonal to the main thread body in FIG. 1B, they need not be and may offset from the main body at non-orthogonal orientations (e.g., 80 or 100 degrees).

Thus, embodiments include inverted threads. An embodiment includes a thread crest that is enlarged and thereby provides a larger surface area for tissue contact. Upon patient loading, where tissue may contact the thread crest with increased force, the larger surface area of the inverted thread may decrease the stress resultant from the load. Pressure points are also lowered due to the reduced stress at those pressure points. This may consequently reduce patient pain. Also, inverted threads include lips that may function to retain tissue within the negative spaces. This may reduce migration. For example, lips 105 and/or 106 protrude out from the thread profile to create an overhang that may hold soft tissues better than traditional thread profiles. Thus, deep negative spaces are possible (which reduce migration) while avoiding sharpened thread crests (which reduces pressure points) that might normally be a by-product of forming such deep negative spaces.

In an embodiment, proximal end 103 is tapered medially (i.e., towards longitudinal axis 124) or inwardly from the main or middle body existing between ends 102, 103. In an embodiment, distal end 102 may be tapered medially from the main body. Due to tapering, the total volume of proximal end 103 may be less than the total volume of distal end 102. Also, when both ends 102, 103 are tapered the maximum diameter 118 (FIG. 1D) for the implant 100 is included in the middle portion of the device (and not in the proximal or distal ends 102, 103). The tapering of one or both ends of implant 100 may result in a capsular shape. With tapered proximal end 103, the resultant reduced trailing edge, which may include softened or rounded edges, may reduce a pressure point or points that interface patient tissue. The turned or "radiused" edge 129 may come in varying sizes such as, for example and without limitation, a range extending generally between 0.1 to 0.3 inches. In various embodiments, there may be between 30, 35, 40, 45, 50, 55, 60, 65, 70 degrees of taper for either or both of the proximal and distal portions. The tapering (e.g., turned edge 129) may facilitate the implant sitting in the sinus tarsi without interference from the lateral prominence on the calcaneus bone.

In an embodiment thread 101 may include aperture 114 directly connected to negative thread space 107 and negative thread space 108. In an embodiment, aperture 114 directly connects to negative thread space 107 at a first location and to negative thread space 108 at a second location, and the first location is separated from the second location by a distance generally less than 1.5 mm This relatively short path helps prevent migration by fostering tissue linking. For example, after receiving the implant a patient may wear a "walking boot" for about two weeks. During that time tissue may grow into spaces in implant 100. By decreasing the length of the void 114, there is a shorter distance for tissue in spaces 107, 108 to traverse void 114 and link together (fully or partially). To the extent this linking is fostered (fully or partially) during the time the patient wears a walking boot (thereby decreasing load transmitted to implant 100); doing so may prevent or lessen migration and patient discomfort.

Figure 1G:
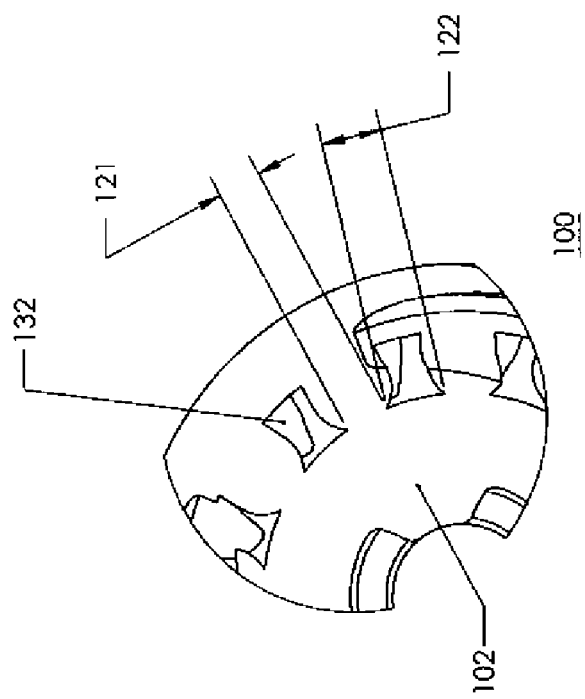
FIG. 1G includes portion 123 of FIG. 1F.

As seen in FIG. 1G, aperture 132 may be tilted. As seen in FIG. 1E, aperture 131 may include central axis 133, passing through aperture 131 without contacting walls of aperture 131. Axis 133 is oblique or non-parallel to longitudinal axis 124. This oblique orientation may provide more available surface area in which to locate apertures, thereby increasing the total number of possible apertures in device 100. In an embodiment, a series of apertures 131, 134, 135, 136, located adjacent multiple thread crests or thread crest portions 137, 138, 139, may align along axis 133.

As seen in FIG. 1B, in an embodiment thread crest 130 is intercepted by horizontal axis 127, which is perpendicular to longitudinal axis 124. Aperture 114 is also intercepted by horizontal axis 127. Aperture 114 is located between thread crest 130 and central hollow bore or shaft 113. Thus, aperture 114 is included in the thread (e.g., main thread body) but is not included in the thread crest 130.

Still concerning FIG. 1B, in an embodiment negative space 140 and negative space 141 are both intercepted by horizontal axis 126, which is perpendicular to longitudinal axis 124. Also, aperture 115 is intercepted by horizontal axis 126 and not connected to central hollow shaft 113.

As seen in FIG. 1F, in an embodiment an aperture includes a lateral wall at radius 119 and a medial wall at radius 120. The differential or distance between the lateral and medial walls may be generally within the range of about 0.01 to about 0.06 inches. This range may provide a width that is small enough to promote tissue in-growth. Making the distance too large may adversely affect the structural integrity of device 100. In various embodiments, the apertures may each generally include dimensions between about 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700 microns per side. In various embodiments the corresponding horizontal cross-sectional area (i.e., cross-sectional area taken on a horizontal plane) may generally include dimensions between about 160,000 to 850,000 square microns.

In various embodiments, a single thread (or multiple threads) may include a range of apertures generally including 2, 5, 10, 15, 20, 25, 30, 35, 40, 45, 50, 55, 60, 60 apertures or more. Also, embodiments may include threads that make various rotations about device 100. For example, in FIG. 1A thread 101 makes three complete revolutions about device 100. In an embodiment, such as with FIG. 1A, thread 101 has a thread crest that is continuous and includes no apertures. However, in other embodiments holes may extend across threads, thereby piercing thread crests (e.g., lips 105, 106). For example, there may be one or more circular horizontal bores extending from one lateral edge of device 100 to the opposite lateral edge. Also, slots may be cut longitudinally across threads and thread crests.

Thus, in various embodiments voids help incorporate tissue for stability and anti-migration properties. The voids may behave like scaffolding for tissue growth. Additionally, the morphology and aperture size may have significant effects on the rate of tissue in-growth. For example, the voids may include a varied shape similar to an hourglass to provide a range of aperture widths. The range of widths may better promote tissue in-growth. For example, an hourglass shape or other shape may mimic that of a reticulated open cell structure as used in cell scaffolds and biologic growth depositions. Use of appropriately sized pores and an interconnected pore structure may promote induction of soft tissue healing and repair. Cell migration, proliferation, and attachment may be influenced by the high surface area presented by shapes such as those found in the hourglass apertures. The irregular crevices, points, and morphology increase surface area and may contribute to cellar strain thereby increasing proliferation as seen in reticulated foams and scaffolds.

Also, the higher number of smaller voids (as opposed to traditional devices with a few vertical slots or horizontally bored voids) provides a high volume for tissue growth but does so using smaller paths for linking (e.g., the small vertical distance of void 114 that links spaces 107, 108), which helps promote faster and more effective tissue in-growth. The small in-growth distance allows for solid, interconnecting chains of tissue to form around struts (e.g., material existing directly between two apertures) of the implant thread, securely anchoring the implant and preventing migration.

FIG. 1D illustrates a "double lead" wherein points 116, 117 connote or define two starting points for two different threads (and corresponding thread crests).

Various embodiments provide for a wide range of dimensions. Dimension 118 generally includes 0.25, 0.30, 0.35, 0.40, 0.45, 0.50, 0.55 inches and beyond (smaller or larger) that particular range. Dimension 119 generally includes 0.10, 0.11, 0.12, 0.13, 0.14, 0.15, 0.16, 0.17, 0.18, 0.19, 0.20, 0.21, 0.22, 0.23, 0.24, 0.25 inches and beyond (smaller or larger) that particular range. Dimension 120 generally includes 0.06, 0.07, 0.08, 0.09, 0.10, 0.11, 0.12, 0.13, 0.14, 0.15, 0.16, 0.17, 0.18, 0.19, 0.20, inches and beyond (smaller or larger) that particular range. Dimension 109 generally includes 0.45, 0.50, 0.55, 0.60, 0.65, 0.70, 0.75 inches and beyond (smaller or larger) that particular range. Dimension 129 generally includes 0.13, 0.14, 0.15, 0.16, 0.17, 0.18, 0.19, 0.20, 0.21, 0.22, 0.23, 0.24, 0.25, 0.26, 0.27, 0.28 inches and beyond (smaller or larger) that particular range. Dimension 112 generally includes 0.030, 0.035, 0.040, 0.045, 0.050, 0.055, 0.060, 0.065, 0.070 inches and beyond (smaller or larger) that particular range.

A method in one embodiment of the invention is now addressed. The method is suitable for use with the various embodiments included in any of FIGS. 1A-H but is not so limited. Embodiments of the invention may include a one-piece titanium alloy (e.g., ASTM F-136) implant comprised of diameters of 7 mm to 12 mm intended for the treatment of hyperpronation. The subtalar implant may be indicated for use in treating the hyperpronated foot and stabilization of the subtalar joint. It may block the forward, downward, and medial displacement of the talus, thus allowing normal subtalar joint motion but limiting excessive pronation.

A user (e.g., doctor) may make a 2-3 cm incision on the lateral aspect of the foot over the sinus tarsi along the relaxed skin tension lines. The user may identify the deep facia and bluntly dissect such allowing entrance into the lateral sinus tarsi. The user inserts the guide pin into the sinus tarsi from lateral to medial until tenting is noted anterior and slightly inferior to the medial maleollus. The user introduces the cannulated probe over the guide pin and into the sinus tarsi with a gentle twisting motion to slightly dilate the tarsal canal. The user removes the cannulated probe and leaves the guide pin in place. The user chooses the appropriate trial device based on the size and anatomy of the patient. The user then introduces the selected cannulated trial device over the guide pin into the sinus tarsi from lateral to medial until the leading edge of the trial device is ⅓ to half way across the subtalar joint. In one embodiment, the leading edge of the trial device may not cross the longitudinal bisection of the talus (i.e., approximately at middle of talus where sinus tarsi narrows considerably) and the trailing edge of the implant may be more than 5 mm medial to the lateral wall of the calcaneous. The appropriate trial device size may limit abnormal calcaneal eversion and may allow approximately 2-4 degrees of subtalar joint eversion.

Once the appropriate size trial device is determined, the user may make note of the depth measurement on the calibrated section of the trial device at the skin line and remove the trial device from the joint while leaving the guide pin in place. The user may place the equivalent size implant (e.g., implant 100) onto the insertion tool and introduce it over the guide pin and thread it into the joint with a clockwise rotation to the predetermined length noted from the depth measurement determined from the trial until clinical correction is noted. The use of intra-operative imaging in the AP and lateral view may be used to verify the final placement of the implant. In an embodiment, the leading edge of the implant may be ⅓ to half way across the subtalar joint and the leading edge of the implant may not cross the longitudinal bisection of the talus while the trailing edge may be more than 5 mm medial to the lateral wall of the calcaneous.

Once the final placement of the implant has been achieved, the user may access the range of motion of the subtalar joint. A significant reduction of excess subtalar joint pronation should be appreciated. The user then removes the insertion tool and the guide pin, irrigates, and then closes the deep tissue, fascia, subcutaneous tissue, and skin layers.

As mentioned above, pressure points are not due solely to sharp or low surface area thread crests and deep negative thread spaces. Some pressure points are due to implant shape. For example, cylindrical/conical implants may include a middle conical section with a smaller cylindrical section at the distal end and a larger cylindrical section at the proximal end. Consequently, the implant may not effectively match the anatomic loading by the talus and calcaneus. For example, in the subtalar joint the calcaneal floor has a slight incline due to a bony prominence. Thus, a flared out implant (e.g., a conical implant) with no or insufficient proximal tapering may contact the bony prominence in a manner that creates a painful pressure point.

Figure 2C:
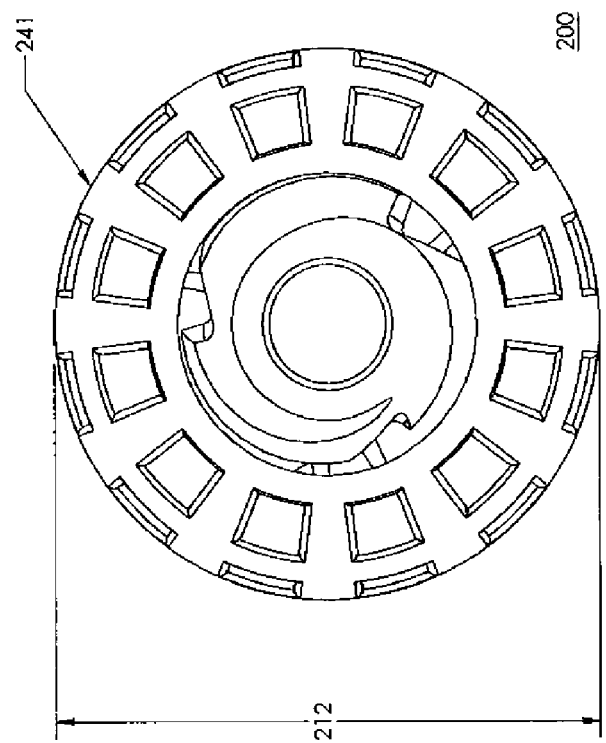
FIG. 2C includes a plan view of one embodiment of the invention.

FIGS. 2A-E, however, include multiple embodiments of the invention with proximal heads that lessen painful pressure points. For example, FIG. 2A includes an embodiment where subtalar implant 200 comprises a main body with middle portion 202 connected to proximal portion 201 and distal portion 203. In FIG. 2D, central hollow shaft 207 extends from proximal portion 201 to distal portion 203 to define longitudinal axis 225. Proximal portion 201 includes spherical portion 204 having a three-dimensional spherical profile with arcuate edge 208. In an embodiment, middle portion 202 may be non-threaded and distal portion 203 may be threaded.

As used herein, "arcuate edge" connotes or describes an arc, arch, or curved edge. An arcuate edge is found in, for example, ellipses. An ellipse includes a curved line where generally the sum of the distances from two points (foci) to every point on the line is constant. The position of the foci determine how "squashed" the ellipse is. A circle is a special case of an ellipse. In an ellipse, if the major and minor axis are the same length then a circle is rendered, with both foci at the center. Embodiments herein may include an arcuate edge in an implant portion that is elliptical. However, other embodiments may include arcuate edges that, while curved and non-linear, may not necessarily constitute portions of an ellipse, such as a circle. Also, as shown in FIG. 2D, elliptical or spherical portion 204 need not be perfectly spherical considering, for example, proximal end 201 couples with middle portion 202. Also, spherical portion 204 may include non-arcuate edges, such as proximal-most end 230, which is non-arcuate (e.g., flattened).

In FIG. 2D, an embodiment has spherical portion 204 that includes many apertures. Aperture 206 is highlighted for ease of description. In an embodiment, aperture 206 does not directly connect to central hollow shaft 207 (however in other embodiments it may do so). In an embodiment, the apertures may connect with each other. For example, in FIG. 2E apertures 219, 220, 221, 222 may couple to one another via a void located inside the spherical portion. For example, aperture 219 may couple to aperture 220 via void or channel 231. Aperture 219 may couple to aperture 222 via void or channel 232. In an embodiment aperture 219 may couple to aperture 220 via void or channel 231 and aperture 219 may couple to aperture 222 via void or channel 232.

As described above regarding, for example, hole 114 of FIG. 1B, the voids or apertures of FIG. 2D may incorporate tissue for stability and anti-migration properties. The apertures may operate like scaffolding. Additionally, the morphology and aperture size, described below, may accelerate tissue in-growth. The voids may include any number of profile shapes including, for example, square, circular, rectangular, and/or hourglass shapes. Hourglass shapes, along with other shapes, may provide a range of aperture widths whose diversity of widths promotes tissue growth. With a greater number of smaller tissue integration voids, a similar or greater total volume of in-growth may be achieved (as compared to traditional designs) while achieving integration at a much faster rate. For example, the small distance (e.g., distance 213) for tissue growth may better foster solid, interconnecting chains of tissue forming in shorter periods of time (e.g., during post-operative periods where a boot is worn) securely anchoring the implant and preventing migration.

In an embodiment, spherical portion 204 may include 10, 15, 20, 25, 30, 35, 40, 45, 50, 55, 60, 65, 70, 75, 80, 85 or more apertures. The apertures may be arranged in a series of rings respectively located on horizontal planes 226, 227 (both orthogonal to longitudinal axis 225) and the like. In an embodiment, apertures (e.g., aperture 206) may include dimensions of about, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700 microns per side. In an embodiment, apertures (e.g., aperture 206) may include a corresponding horizontal cross-sectional area of about 160,000 to 850,000 square microns.

In an embodiment shown in FIG. 2A, distal portion 203 includes maximum diameter 211, which is based on an outer diameter of thread 235. Middle portion 202 includes maximum diameter 236. Spherical proximal portion includes maximum diameter 212 (FIG. 2C). In an embodiment, maximum diameter 211 is larger than maximum diameter 236 but smaller than maximum diameter 212.

Various embodiments provide for a wide range of dimensions. In an embodiment, diameter 211 generally includes 0.12, 0.14, 0.16, 0.18, 0.20, 0.22, 0.24, 0.26, 0.28, 0.30 inches and beyond (smaller or larger) that particular range. Diameter 212 generally includes 0.26, 0.28, 0.30, 0.31, 0.33, 0.35, 0.37, 0.39, 0.41, 0.43, 0.45, 0.47, 0.49, 0.51 inches and beyond (smaller or larger) that particular range. Diameter 236 is generally 0.02 to 0.08 inches smaller than diameter 211. Length 209 generally includes 0.59, 0.61, 0.63, 0.65, 0.67, 0.69, 0.71, 0.73, 0.75, 0.77, 0.79, 0.81, 0.83, 0.85, 0.87, 0.89, 0.91, 0.93 inches and beyond (smaller or larger) that particular range. Length 210 generally includes 0.26, 0.28, 0.30, 0.31, 0.33, 0.35, 0.37, 0.39, 0.41, 0.43, 0.45, 0.47, 0.49, 0.51 inches and beyond (smaller or larger) that particular range. Distance 237 generally includes 0.02, 0.03, 0.04, 0.05, 0.06 inches and beyond (smaller or larger) that particular range. Distance 213 generally includes 0.02, 0.03, 0.04, 0.05, 0.06 inches and beyond (smaller or larger) that particular range. Distance 214 generally includes 0.02, 0.03, 0.04, 0.05, 0.06 inches and beyond (smaller or larger) that particular range. Embodiments may include various materials such as steel, titanium alloy (e.g., ASTM F-136), medical grade polymer, and the like.

As seen in FIG. 2A, in an embodiment arcuate edge 208 has arc 240 extending at least 100° in a longitudinal plane parallel to longitudinal axis 225. Other embodiments are not so limited and may have arcs extending, for example, 60, 65, 70, 75, 80, 85, 90, 95, 105, 110, 115° and beyond (smaller or larger) that particular range. For example, some embodiments may include no flattened top 230 and may instead extend edge 208 across the proximal end and back to middle portion 202, thereby extending, for example, 270, 275, 280, 285, 290, 295, 300, 305, 310, 315° and beyond (smaller or larger) that particular range.

Figure 2B:
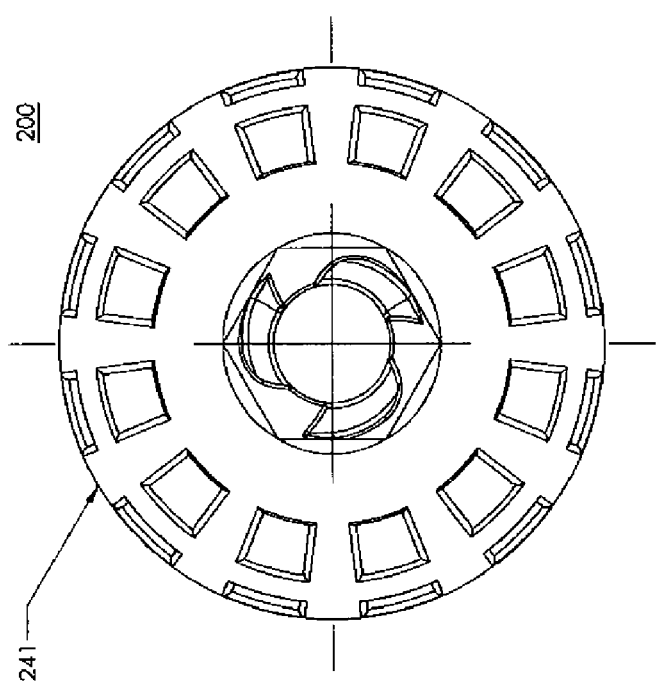
FIG. 2B includes a plan view of one embodiment of the invention.

As seen in FIGS. 2B and 2C, embodiments of the invention may include arcuate edge 241 that is circular and extends 360° in a horizontal plane orthogonal to longitudinal axis 225.

Embodiments of the invention may combine elements from (for example) FIGS. 1B and 2D. For example, while not shown in a figure, a thread (e.g., thread 205) of implant 200 may include an inverted thread. Specifically, as described more fully above in regards to various embodiments in FIGS. 1A-H, a thread may be included in distal portion 203 and revolve about the distal portion. A first negative thread space may be located distal and directly adjacent to the first thread crest portion and a second negative thread space may be located proximal and directly adjacent to the first thread crest portion. The first thread crest portion may include a first lip projecting across a lateral portion of the first negative thread space and a second lip, opposite the first lip, may project across a lateral portion of the second negative thread space. In an embodiment, the thread may include an aperture directly connected to both the first negative thread space and the second negative thread space. In an embodiment, the first aperture may be included in the first thread but not in the thread crest.

Figure 2E:
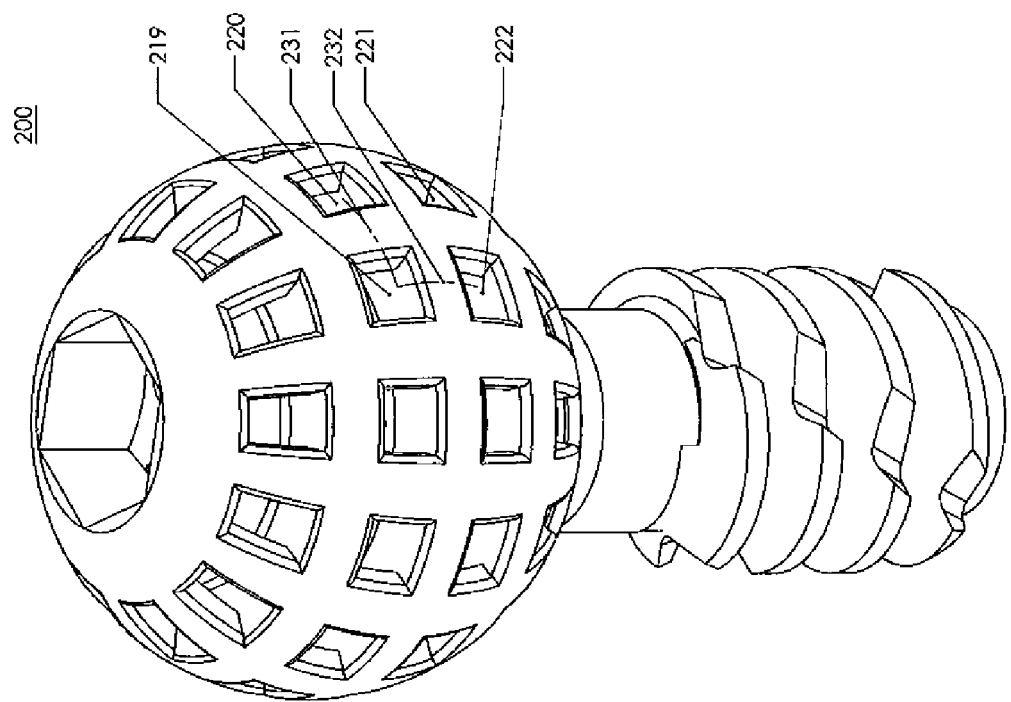
FIG. 2E includes a perspective view of one embodiment of the invention.
Figure 3:
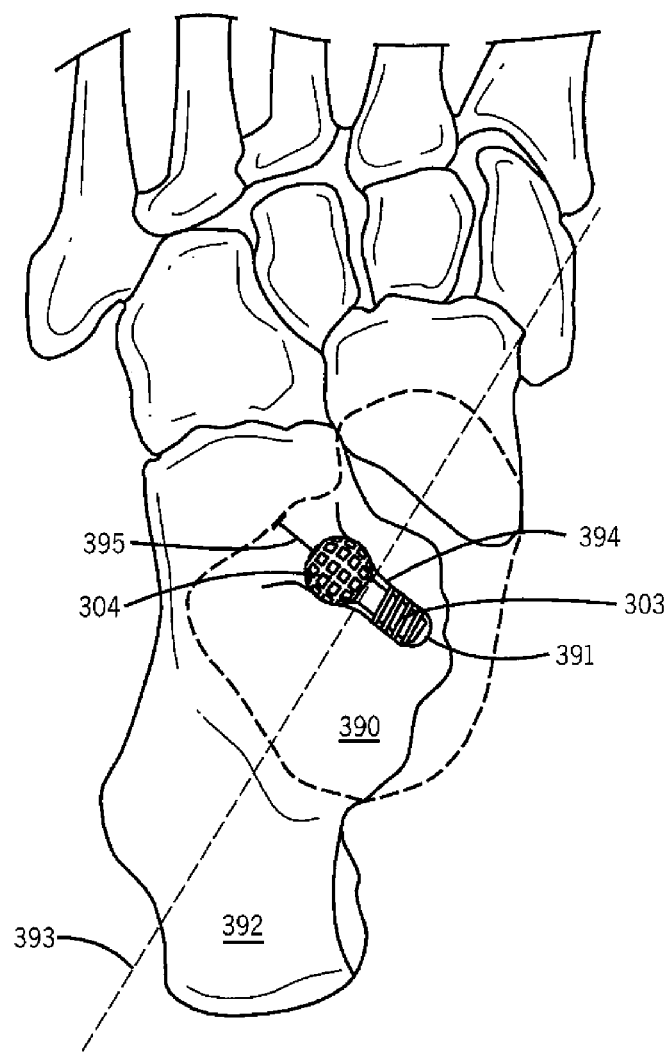
FIG. 3 includes a view of an embodiment of the invention implanted in a foot.

Various embodiments include methods for implanting devices such as implant 200 of FIG. 2E. In one embodiment, implant 200 of FIG. 2E is screwed into a sinus tarsi of a patient. In FIG. 3, distal portion 303 of the implant may be proportioned to implant past the longitudinal bi-section 393 of the talus 390 (i.e., approximately at the middle of talus 390 where the sinus tarsi 394 narrows considerably) and into the deeper canalis portion 391 of sinus tarsi 394. Spherical proximal portion 304 may abut the entry to deeper canalis 391, thereby providing motion blocking. The user may directly connect a first arcuate edge, located on an elliptical proximal portion 304 of the implant, to the talus 390 of the patient at a first contact point. The user may also directly connect a second arcuate edge, also located on an elliptical proximal portion 304 of the implant, to the calcaneus 392 of the patient at a second contact point.

In an embodiment, the user may locate the proximal-most end of the implant a distance 395 that is lateral (e.g., 0 to 3 mm) or medial (e.g., 0 to 3 mm) from the lateral edge of the talus 390 upon final implantation. Considering the trailing edge of the implant may now have more contact with bone due to the implant's deep insertion, the elliptical proximal portion (e.g., spherical) may help mitigate pressure points associated with contact near the trailing edge of the implant.

During implant and immediately thereafter, the elliptical shape of the proximal portion of the implant (e.g., head or head region) may provide a uniform bearing surface at any angle of contact between the talus and calcaneus to provide uniform block of the joint motion while also preventing stress points that may be attributed to hard edges. The curved portion may help accommodate certain anatomical features such as the calcaneus bony prominence on the floor of the sinus tarsi. In contrast, a conical implant may not provide uniform block of joint motion due to, for example, anatomical considerations (e.g., calcaneus bony prominence) and/or physician implant technique. For example, if the conical implant is implanted at too steep an angle, a sharp proximal edge of a conical section may place undue pressure on the talus. If the conical implant is implanted at too shallow an angle, a sharp proximal edge of a conical section may put undue pressure on the calcaneous.

Thus, with certain embodiments in a first position the arcuate edge will have a first incident angle or angle of contact with the calcaneus of the patient. But even if the angle of insertion changes (due to user choice, settling, migration, or the like) and the implant is partially rotated about a horizontal axis of the implant or shifts along the longitudinal axis of the implant (e.g., due to user choice, migration, and the like) the arcuate edge would still maintain the first angle of contact with the calcaneus of the patient. This may provide a margin of error for implantation, migration, and the like.

Also, due to the elliptical shape (e.g., ovular, spheroid) of the proximal portion of the implant, even if the implant settles or changes position over time, the angle of contact between the talus and the elliptical section and the angle of contact between the calcaneus and the elliptical section will not necessarily change.

Consequently, the risk for present (at time of implantation) and future (days, weeks, or years after implantation) pressure points is diminished. This may decrease damage to the bone (which may occur due to the implant material being harder than bone) and/or patient pain.

A method in one embodiment of the invention is now addressed. The method is suitable for use with various embodiments in FIGS. 2A-E but is not so limited. A user may make a 2-3 cm incision on the lateral aspect of the foot over the sinus tarsi along the relaxed skin tension lines. The user may identify the deep facia and bluntly dissect such allowing entrance into the lateral sinus tarsi. The user inserts the guide pin into the sinus tarsi from anterior lateral to posterior medial until tenting is noted slightly posterior to the medial maleollus. The user chooses an appropriate trial device based on the size and anatomy of the patient. The user may introduce the selected cannulated trial device over the guide pin into the sinus tarsi and canalis tarsi from anterior lateral to posterior medial until the trial will not advance anymore. The appropriate trial size should limit abnormal calcaneal eversion and may allow approximately 2-4 degrees of subtalar joint eversion.

The user then places the equivalent size implant onto the insertion tool and introduces it over the guide pin and threads it into the joint with a clockwise rotation. Once the implant has been advanced 3-4 full turns into the canalis tarsi, the user removes the guide pin and fully seats the implant until it does not advance any further and final placement matches the predetermined length noted from the depth measurement determined from the trial until clinical correction is noted. The use of intra-operative imaging in the AP and lateral view may verify the final placement of the implant. In an embodiment, the trailing edge of the implant may sit +/−2 mm from the neck of the talus.

Once the final placement of the implant has been achieved, the user may assess the range of motion of the subtalar joint. A significant reduction of excess subtalar joint pronation should be appreciated. The user may then irrigate and close the deep tissue, fascia, subcutaneous tissue, and skin layers.

While embodiments of the invention have been mentioned in terms of a subtalar implant, claim scope is not necessarily so limited. Embodiments are suitable for other implantation sites, such as other joints, bones (of the foot and elsewhere in the body), humans and other animals, and the like. Several embodiments are described as being cannulated but other embodiments may be uncannulated with no central hollow shaft. Embodiments may include various materials such as steel, titanium alloy (e.g., ASTM F-136), medical grade polymer (e.g., high molecular weight polyethylene, PEEK, PEKK, PMMA, PTFE), and the like. Also, while the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. A subtalar implant comprising:
   a main body including a middle portion connected to a proximal portion and a distal portion, the distal portion configured to insert into a sinus of a patient before the proximal portion; and
   a central hollow shaft included in the main body and extending from the proximal end to the distal end to define a longitudinal axis and form a tunnel that extends completely through the main body;
   wherein the proximal portion includes a generally spherical portion having a three-dimensional spherical profile with an arcuate edge;
   wherein the spherical portion includes a plurality of apertures that (a) do not directly connect to the central hollow shaft, but (b) do couple with each other via a void, which is not coterminous with the central hollow shaft, located inside the spherical portion.

2. The implant of claim 1, wherein the middle portion is non-threaded and the distal portion is threaded.

3. The implant of claim 1, wherein the plurality of apertures includes more than 15 apertures arranged in a series of rings respectively located on a series of horizontal planes that are each orthogonal to the longitudinal axis.

4. The implant of claim 1, wherein each of the plurality of apertures includes a horizontal cross-sectional area between about 160,000 and 850,000 square microns.

5. The implant of claim 1, wherein (a) the distal portion includes a first maximum diameter, which is based on an outer diameter of a thread included in the distal portion, the middle portion includes a second maximum diameter, and the spherical portion includes a third maximum diameter, (b) the first maximum diameter is larger than the second maximum diameter but smaller than the third maximum diameter, and (c) the distal portion is proportioned to implant within the deeper canalis portion of the sinus tarsi of the patient.

6. The implant of claim 1, wherein the arcuate edge has an arc extending at least 100° in a longitudinal plane parallel to the longitudinal axis.

7. The implant of claim 6, wherein the spherical portion includes an additional arcuate edge that is circular and extends 360° in a horizontal plane orthogonal to the longitudinal axis.

8. The implant of claim 7, wherein the spherical portion includes a proximal-most end that is non-arcuate and coterminous with the proximal-most end of the implant.

9. The implant of claim 1 comprising:
 a first thread included in the distal portion and revolving about the distal portion, the first thread including a first thread crest portion;
 a first negative thread space located distal and directly adjacent to the first thread crest portion;
 a second negative thread space located proximal and directly adjacent to the first thread crest portion;
 wherein the first thread crest portion includes a first lip projecting across a lateral portion of the first negative thread space and a second lip, opposite the first lip, projecting across a lateral portion of the second negative thread space.

10. The implant of claim 9, wherein the first thread includes a first aperture directly connected to both the first negative thread space and the second negative thread space.

11. The implant of claim 10, wherein the first aperture is included in the first thread but is not included in the first thread crest portion.

12. The implant of claim 1, wherein the spherical portion includes an additional arcuate edge that is circular and extends 360° in a horizontal plane orthogonal to the longitudinal axis.

13. The implant of claim 1, wherein (a) in a first position the spherical portion is configured to contact the calcaneus of the patient at a first location at a first angle of contact, and (b) in a second position, where the implant is rotated less than 360° about a horizontal axis orthogonal to the longitudinal axis, the spherical portion is configured to contact the calcaneus at a second location yet still maintain the first angle of contact with the calcaneus based on the shape of the arcuate edge.

14. A method comprising:
 providing a subtalar implant including (a) a main body comprising a middle portion, which is connected between a proximal portion and a distal portion, and (b) a central hollow shaft included in the main body and extending from a proximal end to a distal end to define a longitudinal axis and form a tunnel that extends completely through the main body; (c) wherein (c) (1) the proximal portion includes a generally spherical portion having a three-dimensional spherical profile with an arcuate edge; and (c) (2) the spherical portion includes a plurality of apertures that do not directly connect to the central hollow shaft, but do couple with each other via a void, which is not coterminous with the central hollow shaft, located inside the spherical portion;
 screwing the distal portion past a longitudinal bi-section of a talus of a patient and into a deeper canalis portion of the sinus tarsi of the patient;
 directly connecting the spherical portion to the talus of the patient at a first contact point; and
 directly connecting the spherical portion to the calcaneus of the patient at a second contact point.

15. The implant of claim 6, wherein the arc has a midpoint located at the maximum diameter of the proximal portion and half of the arc is proximal to the midpoint and the other half of the arc is distal to the midpoint.

\* \* \* \* \*